United States Patent [19]

Buysch et al.

[11] Patent Number: 5,750,801
[45] Date of Patent: May 12, 1998

[54] PROCESS FOR THE CONTINUOUS PREPARATION OF BENZYL ALCOHOL

[75] Inventors: Hans-Josef Buysch; Ursula Jansen; Pieter Ooms, all of Krefeld; Erhard-Günther Hoffmann, Ratingen; Bernd-Ulrich Schenke, Bottrop, all of Germany

[73] Assignee: Bayer Aktiengesellschaft, Leverkusen, Germany

[21] Appl. No.: 767,729

[22] Filed: Dec. 16, 1996

[30] Foreign Application Priority Data

Dec. 27, 1995 [DE] Germany .................. 195 48 876.8

[51] Int. Cl.$^6$ ..................................... C07C 33/18
[52] U.S. Cl. ............................................ 568/715
[58] Field of Search ............................. 562/715

[56] References Cited

U.S. PATENT DOCUMENTS 4,474,993 10/1984 Goran .

FOREIGN PATENT DOCUMENTS

| 0064486 | 11/1982 | European Pat. Off. . |
| 0768291 | 4/1997 | European Pat. Off. . |
| 19520612 | 12/1996 | Germany . |

*Primary Examiner*—Samuel Barts
*Attorney, Agent, or Firm*—Sprung Kramer Schaefer & Briscoe

[57] ABSTRACT

The invention relates to a process for the preparation of benzyl alcohol by hydrolysis of benzyl chloride with water at elevated temperatures, which avoids any wastewater pollution.

1 Claim, 3 Drawing Sheets

PROCESS FOR THE CONTINUOUS PREPARATION OF BENZYL ALCOHOL

The present invention relates to a process for the preparation of benzyl alcohol by hydrolysis of benzyl chloride with water at elevated temperatures, characterized in that water and benzyl chloride are continuously fed into a reactor having dispersion devices, the reaction product, after incomplete conversion, is separated into an organic phase and aqueous phase, the organic phase is continuously fed into a first distillation column and fractionated into benzyl chloride, which returns to the reactor, and crude benzyl alcohol which emerges from a second distillation unit as pure benzyl alcohol in addition to a by-product-containing bottom phase, the aqueous hydrochloric acid-containing phase is treated in a continuous extraction apparatus with a solvent which takes up the organic materials dissolved in water, particularly benzyl alcohol, the extract, in a third distillation unit, is freed from the solvent which returns to the extraction apparatus, the bottom phase of the third distillation unit is fed into the first distillation apparatus and the hydrochloric acid-containing aqueous phase after the extraction is passed to a hydrogen chloride absorption unit in order to concentrate it with respect to hydrogen chloride and supply it to a further use or feed it to a hydrochloric acid electrolysis for chlorine production.

A great deal has already been reported on the hydrolysis of benzyl chloride. Many publications deal with this problem to elucidate the reaction mechanism and develop analytical methods. In this earlier work, homogeneous mixture of benzyl chloride, water and a water-soluble solubilizer such as alcohol, acetone, dioxane or acetic acid are generally used; see, e.g. J. Chem. Soc. 1954, 1840 ff; Z. Naturf. 1946 (1) 580–4, J. Chem. Soc. 1957, 4747 ff, Tetrahedron 1957 (1) 129–144; Rec. 48, 227 ff (1929) and 49, 667 ff (1930). In various cases, the hydrolysis is also performed in the presence of alkali metal hydroxides, alkali metal carbonates or alkaline earth metal carbonates, such as in J. Am. Chem. Soc. 62, 2481 (1940), Rec 53, 891 ff and 869 ff (1934), the latter publications indicating that the hydrolysis is accelerated in the presence of basic compounds. In all of these earlier works, no importance is attached to the isolation and identification of the hydrolysis products.

However, there are also studies of the hydrolysis of benzyl chloride with water alone which include a description of the hydrolysis products. According to Ann. 139 ff (1866), benzyl chloride is primarily converted into hydrocarbons and dibenzyl ether at 190° C. with water.

Under milder conditions (Ann. 196, 353 (1879), at 100° to 110° C. and with complete conversion, a yield of benzyl alcohol of 76% of theory is obtained—although at very high dilution; the remainder was high-boilers, which were not characterized.

The finding that the reaction proceeds faster and more smoothly in the presence of alkalis led to early attempts in the industrial sector to neutralize the hydrochloric acid formed during the hydrolysis of benzyl chloride. Thus, DRP 484 662 recommends carrying out the reaction in the presence of calcium carbonate, and in U.S. Pat. No. 2,221,882, the procedure is carried out firstly in the presence of a soda solution and then a sodium hydroxide solution. The yield is significantly above 90% of theory.

Sodium carbonate apparently proved itself in practice as a base and was retained afterwards. Further developments in this area are concerned with the technical development of this basic hydrolysis of benzyl chloride as a continuous process as described in German Offenlegungsschrift 2 101 810, EP-A 64 486 and DD Patent Specification 161 067.

However, disadvantages of the alkaline hydrolysis are the additional use of sodium carbonate, the formation of sodium chloride and the production of large amounts of aqueous waste liquors which must be disposed of.

The object of the present invention was therefore to develop a novel process which avoids the addition of sodium carbonate and thus the production of common salt and wastewater loading.

It has now been found that this can virtually be achieved with at least the same or better yield of benzyl alcohol if benzyl chloride is reacted with 10 to 70 times the molar amount of water with intensive mixing at temperatures between 80° C. and 180° C. and converted incompletely.

According to the prior knowledge, the result was in no way to be expected: the yields which had been disclosed hitherto were moderate and the nature of the by-products was not known. The 76% of benzyl alcohol obtained under mild conditions at 100° C. to 110° C. (Ann. 196, 353 (1879)) were produced at a molar ratio of $H_2O$: benzyl alcohol of 190:1, that is a weight ratio of 27:1; this means that although the resulting hydrochloric acid on the one hand had a very low concentration and therefore could scarcely initiate by-product formation, on the other hand it also had no usable value.

Furthermore, under these conditions, an industrially unacceptably low space-time yield was to be expected.

On the other hand, with a reduction of the molar ratio below 190:1 to the claimed values of 10 to 70:1, a markedly increased by-product formation had to be expected, because the hydrochloric acid concentration and thus its activity increases several fold.

In contrast, the process of the invention gives a hydrochloric acid of higher concentration as by-product which can be further used.

A suitable starting product for the process of the invention is benzyl chloride, as is generally available by side-chain chlorination.

Obviously, suitable compounds are also benzyl chloride substituted with halogen such as chlorine, with carboxyl, cyano, methoxy, methyl and nitro. Preference is given to unsubstituted benzyl chloride, however.

The process of the invention for the preparation of benzyl alcohol by hydrolysis of benzyl chloride with water at elevated temperature is characterized in that a) benzyl chloride and water are continuously fed into a reactor containing dispersion devices in a molar ratio of 1:(10 to 70), in which reactor a temperature of 80° to 180° C. prevails, and are reacted therein up to a benzyl chloride conversion rate of 30 to 90%.

b) the reaction product, after exiting the reactor, is separated into an aqueous and organic phase, c) the organic phase is separated in a first distillation apparatus into benzyl chloride and crude benzyl alcohol, d) this benzyl chloride is recycled to the reactor, e) the crude benzyl alcohol is refined in a second distillation unit to give high-purity benzyl alcohol, a bottom phase containing the by-products (particularly dibenzyl ether) being produced, f) the aqueous phase from the separator containing dilute hydrochloric acid is treated in an extraction apparatus with a solvent which takes up the organic constituents, particularly benzyl alcohol, which are still dissolved in the dilute hydrochloric acid, g) in a third distillation apparatus, this extract is freed of solvent which returns to the extractor, h) the bottom phase from the third distillation is passed to the first, in order to recover the benzyl alcohol therefrom and i) the dilute aqueous hydrochloric acid from the extraction, after taking off residual organics, is passed into an HCl absorption unit in order to concentrate it and feed it as high-purity hydrochloric acid to further use or to hydrochloric acid electrolysis for chlorine production for toluene side-chain chlorination.

BRIEF DESCRIPTION OF DRAWINGS

The process of the invention is depicted by way of example in FIG. 1. The temperature in the reactor (R) is 80°–180°, preferably 100°–170°, particularly preferably 110°–150° C. The reactor can be operated isothermally, by removing the heat of reaction by cooling, or else, advantageously, adiabatically, by introducing (1) the starting materials E (BCl=benzyl chloride and $H_2O$) via the mixer (M) at a temperature such that the reaction mixture in the reactor heats up to the desired reaction temperature and also leaves (2) the reactor at this temperature.

The molar ratio of benzyl chloride (BCl) to water ($H_2O$) is 1:10 to 1:70; preferably 1:15 to 1:55, particularly preferably 1:20 to 1:50, very particularly preferably 1:25 to 1:50.

The conversion of benzyl chloride is expediently terminated at 35 to 90%, preferably at 40 to 85%, particularly preferably 45 to 80%.

The reactor (R) used can be a simple stirred tank, which is able to disperse the reaction mixture finely under the reaction conditions.

However, more expediently, a stirred-tank cascade of 2 to 7, preferably 3 to 5, tanks is used.

Figure 2:
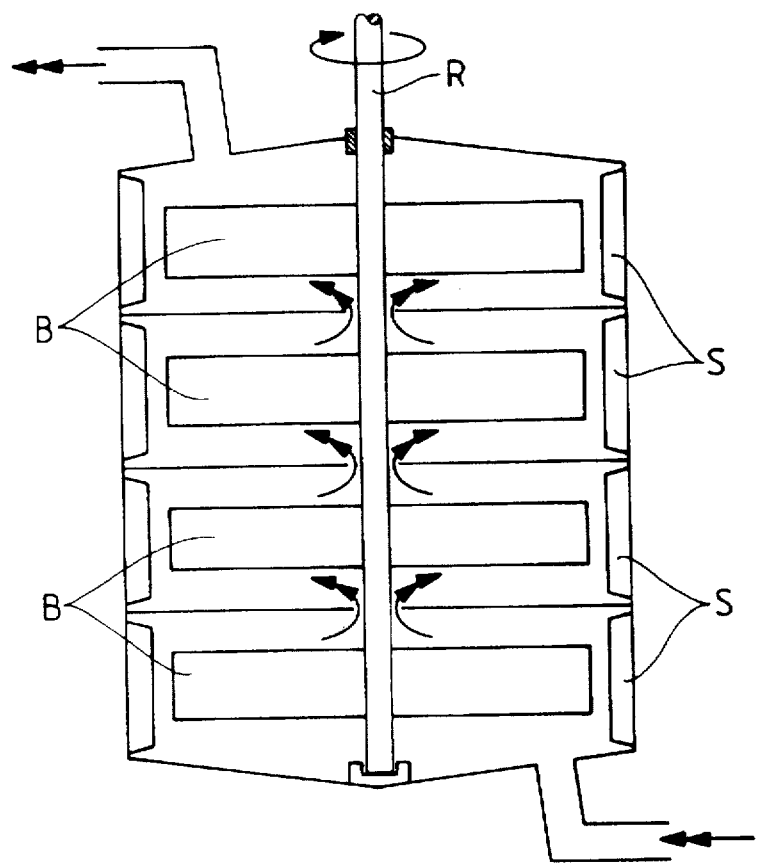
Figure 3:
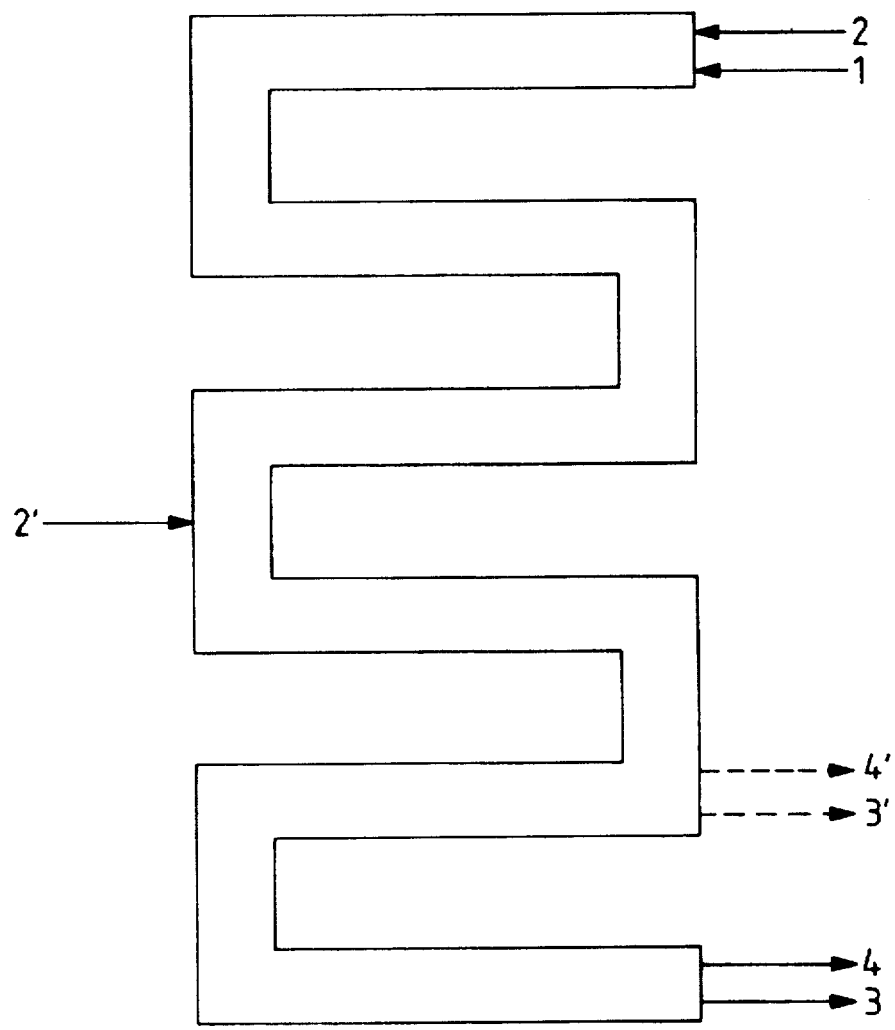

Advantageously, use is also made of chamber reactors (FIG. 2 as example), in which the individual chambers (K) are agitated by an agitator (R), which carries 2–4 blades (B) per chamber, and which are equipped with 2 or more flow baffles (S) per chamber for improved dispersion and are directly connected to one another without significant back-mixing (exemplary course of a flow of the two-phase mixture) being able to occur (cf. FIG. 2), having 2 to 10, preferably 3 to 8, particularly preferably 3 to 6, chambers, and tubular reactors (FIG. 3), through which the reaction mixture flows in a plug-like manner with sufficient velocity for the formation of a turbulent state, and in which benzyl chloride can be very finely distributed in water by known mixing and dispersion elements. In this case, the reaction mixture of organic phase (1) and aqueous phase (2) can be supplemented (2') at any desired points of the tubular reactor, and the reaction mixture of benzyl chloride and benzyl alcohol (3) and dilute hydrochloric acid (4), depending on the residence time, can be taken off at the end of the reactor or else in advance (3' and 4'). Tubular reactors of this type can be designed and constructed by those skilled in the art according to known methods (Perry's Chemical Engineers Handbook, McGraw Hill N.Y., 6th Ed. 1984).

The droplet diameter of the organic phase dispersed in the water can be, for example, 100–400 μm, preferably 150–300 μm.

If the reaction is carried out at temperatures >100° C., pressure resistant apparatuses must be used up to about 50 bar, preferably 30 bar, particularly preferably 20 bar.

The reaction mixture (2) leaving the reactor is expediently separated (T1) at elevated temperature between 50° and 100°, preferably 55° and 95°, into an organic phase and an aqueous dilute hydrochloric acid, the concentration of which depends on the molar ratio of the reactants at the outset and the conversion rate achieved and is, for example, 2 to 7% by weight of HCl. The phase separation can, if appropriate, be markedly accelerated by using separators such as coalescers, which are described, for example, in Ullmann's Encyclopedia of Ing. Chem. Unit Operations II Vol. B3 pp. 6–31 and Chem. Ing. Techn. (1986) 58, 449 ff.

If the reaction is carried out at temperatures >100° C., e.g. 130° C., the reaction mixture can be cooled down prior to entry into the separator (T1) by flash evaporation (2'→EV→3'). In this case, some of the unreacted benzyl chloride and some of the water can be evaporated from the reaction mixture and recycled to the reactor (16'). In this manner, energy for heating up the starting materials and cooling liquid for the reaction mixture can be saved and the resulting dilute hydrochloric acid can be somewhat concentrated.

It is also advantageous to effect the cooling of the reaction product (2) upstream of the separator (T1) by removing the excess heat in a heat exchanger (WT) and thus reheating the aqueous phase (6) leaving the extractor (Ex) either by direct exchange (via 6'→6") in a heat exchanger (WT) or via a thermal transport medium circuit (WK), in order to remove, at least in part, residual organic material (8) from the aqueous phase by taking it off (V).

The organic phase (4) flowing from the separator (T1) predominantly contains benzyl alcohol and benzyl chloride, dibenzyl ether as by-product and small amounts of dilute hydrochloric acid still in solution. The ratio of the organic materials to one another is determined by the conversion rate achieved in the reactor. The content of benzyl alcohol can be, for example, 40–75%, of dibenzyl ether 0.5–6%, and hydrochloric acid 0.5–8%.

Separating these mixtures by distillation (D1) is not obvious, since at elevated temperature, by-products, particularly dibenzyl ether, can be formed from benzyl chloride and benzyl alcohol and from benzyl alcohol and hydrochloric acid. These condensations, according to the literature, also proceed during the work-up by distillation of a hydrolysis mixture of this type, as soon as the content of benzyl chloride is above 1% (Chem. Prum. 32 (1982), 586; cited in C.A. 98 106 890). In order to suppress the subsequent formation of dibenzyl ether which occurs during the distillation, complex reaction of residues of benzyl chloride with nitrogen compounds, for example with hexamethylenetetramine, is recommended (CS 216 042 B; cited in C.A. 102, 45606t). The separation of a mixture which contains benzyl chloride, benzyl alcohol, dibenzyl ether and aqueous hydrochloric acid succeeds according to the invention by the fact that a mixture of this type is fed via a side feed to a continuously operating distillation column having a stripping section and an enrichment section, the distillation column is operated at a pressure of 1–950 mbar at the top of the column and a mixture which essentially comprises benzyl chloride and aqueous hydrochloric acid is taken off at the top of the distillation column and a mixture which essentially comprises benzyl alcohol and dibenzyl ether is taken off from the bottom of the distillation column.

Therefore, the mixture (4) leaving the separator (T1) is fed into the side of a first distillation column (D1). This is operated at a pressure of 1–950 mbar, preferably 10–500 mbar, particularly preferably 20–300 mbar at the top of the column. In this case, in a manner known to those skilled in the art, a temperature in the bottom phase of 30°–200° C., preferably 60°–180° C., particularly preferably 70°–165° C., is established as a function of the overhead pressure set and as a function of the composition of the mixture to be separated. In a corresponding manner, an overhead temperature of 20°–175° C., preferably 50°–155° C., particularly preferably 60°–140° C., is established. The overhead temperature in this case is always below the bottom phase temperature. The side feed to be preferred of the mixture to be separated is carried out at a point of the distillation column at which a temperature of 25°–195° C., preferably 55°–175° C., particularly preferably 65°–160° C., prevails. The establishment of a temperature gradient is known to those skilled in the art. It is dependent, inter alia, on the composition of the mixture and on its preheating. The distillation column can be operated with a loading of 0.05–1.0 kg of organic phase in the mixture to be separated per liter of a void volume of the column per hour. Preferably, a loading of 0.15–0.9 kg/l –h, particularly preferably 0.25–0.8 kg/l –h, is set.

The additional formation of dibenzyl ether is virtually prevented according to the invention and is reduced to low values of less than 4%, preferably less than 2%, particularly preferably less than 0.5%, based on the amount of benzyl alcohol.

At the top of the column (D1), a mixture (16) of the total unreacted benzyl chloride and the total hydrochloric acid still in solution is taken off which returns to the reactor (R), and at the foot of the column a crude benzyl alcohol (17) which virtually no longer contains benzyl chloride, but contains all the high-boilers, particularly dibenzyl ether, is taken off.

The column can be equipped with the known internals such as bubble-cap trays, sieve trays and other tray structures, with packings of various types or else, particularly, arranged packings.

The bottom phase (17 or 17') of this column (D1) is conveyed into a second distillation unit which can comprise one (D2") or two (D2+D2') distillation columns. If only one column (D2") is used, the bottom product (17) from the benzyl chloride distillation (D1) must be virtually free of low-boilers, in particular free of benzyl chloride. At the top of this column (D2"), high-purity benzyl alcohol (BA 21') having a content >99.99% is taken off, and from the bottom phase, the high-boiler mixture (20') is taken off which essentially comprises dibenzyl ether (DB), residual benzyl alcohol and a small amount of other high-boiling material and which can, if appropriate, be further worked up batchwise.

However, if the second distillation unit comprises two columns (D2+D2'), the crude benzyl alcohol (17) can further be freed from small amounts of low-boilers (18), particularly of benzyl chloride, in the first (D2) column, in the second (D2') column, the low-boiler-free crude benzyl alcohol (19) is then fractionated into high-purity benzyl alcohol (21) and bottom products (20), as already described above.

Non-condensable low-boilers and off-gases (22'–22'$^{IV}$) can be taken off from the distillation columns and disposed of in an off-gas combustion unit (AG), for example.

The columns D2–D2" are operated at a reduced pressure of 500–10 mbar, preferably 250–10, particularly preferably 100–10 mbar.

The dilute hydrochloric acid (5) obtained in the separator (T1) after the reaction (2) is treated in an extraction device (Ex) with a suitable solvent, in order to obtain the organic constituents dissolved in the aqueous phase—principally benzyl alcohol which, depending on conditions, dissolves in the dilute hydrochloric acid (5) at approximately 2–4%, and also benzyl chloride, although this is dissolved to a lesser extent. The temperature in the extraction (Ex) is 20–100, preferably 40–95, particularly preferably 50°–95° C.

Suitable solvents are hydrocarbons having 4 to 9 carbon atoms, halogenated hydrocarbons having 1 to 8 carbon atoms, preferably aromatic hydrocarbons such as benzene, toluene, xylenes, ethylbenzene and cumene, halogenated hydrocarbons such as methylene chloride, chloroform, dichloroethane, trichloroethylene, chlorobenzene and benzyl chloride; particular preference is given to toluene and benzyl chloride.

If losses of solvent (L) occur, they can be (14') restored into the extraction.

The extraction (Ex) is carried out continuously in countercurrent in known apparatuses, as are described, for example, in Ullmann's Encyclopedia of Ind. Chem. Unit. Oper. II Vol. B3, pp. 6–14 ff. Those which may be mentioned are packed columns, tray columns, pulsed tray columns, pulsed arranged-packing columns, mixer-settler batteries, columns containing rotating internals, and centrifugal extractors.

The extract (13) is freed from extraction medium and traces of the dilute hydrochloric acid in a third distillation column (D3), the top product (14) is returned to the extraction apparatus (Ex) and the bottom phase (15) from this column (D3), together with (4), is fed into the first distillation column (D1), where benzyl alcohol and benzyl chloride are separated. This third distillation column (D3) operates at 750–50, preferably 500–150, and particularly preferably 400–200, mbar.

The dilute aqueous hydrochloric acid (6) from the extractor (Ex) is used to operate, in a known manner, an HCl absorption unit (AS) in which, for example, hydrogen chloride (11) from a toluene chlorination or aromatics chlorination is converted into a high-strength hydrochloric acid (12), which is very pure and is suitable for other technical applications or electrolytic work-up to give chlorine.

Before the dilute hydrochloric acid (6) is passed from the extraction (Ex) into the absorption unit (AS), residues present therein of organic compounds which, originating from the extraction (Ex), are still dissolved in hydrochloric acid (6), such as toluene, benzyl chloride or traces of benzyl alcohol, should be separated off to the greatest possible extent by stripping (V). The dilute hydrochloric acid (7) virtually free from organics is then completely freed from traces of carbon compounds in the absorption (AS) by distillation and the distillate (8') is separated in a separator (T2) into water and organics.

As already described, the stripper (V) is supplied with the waste heat from the reaction mixture (2) via heat exchange (WT directly or via WK). A mixture (8) of predominantly water and little organic material leaves the stripper, which mixture, together with the mixture (8') of water and organic residues possibly coming from the absorption (AS), is separated in the separation vessel (T2) into an aqueous phase and an organic phase. The aqueous phase (9) returns via (M) to the reaction (R), the organic phase (10) can be fed into a toluene chlorination or back into the third distillation column (T3).

In this manner, a continuous process for the preparation of benzyl alcohol from benzyl chloride hydrolysis with water is carried out which does not require any bases, produces neither salts nor waste liquors which must be disposed of, nor significant amounts of organic waste products, since dibenzylether can either be used directly industrially, for example in the rubber industry, or else, together with the other high-boilers (20+20') and the organic compounds (10) from the separation vessel (T2), can be further reacted with chlorine to give benzotrichloride and benzoyl chloride in a toluene chlorination.

Benzyl alcohol is an important product, which is increasing in importance because of its extremely low toxicity, for the preparation of perfumes, cosmetics, paints, plasticizers and is a sought-after auxiliary for the rubber, paints and textile industries.

The percentages in the following examples are in each case by weight; parts are parts by weight.

EXAMPLE

Benzyl chloride and water were reacted with one another in a molar ratio of 1:35 at 130° C., the reaction was terminated at a benzyl chloride conversion rate of 60% and the reaction mixture was worked up.

Figure 1:
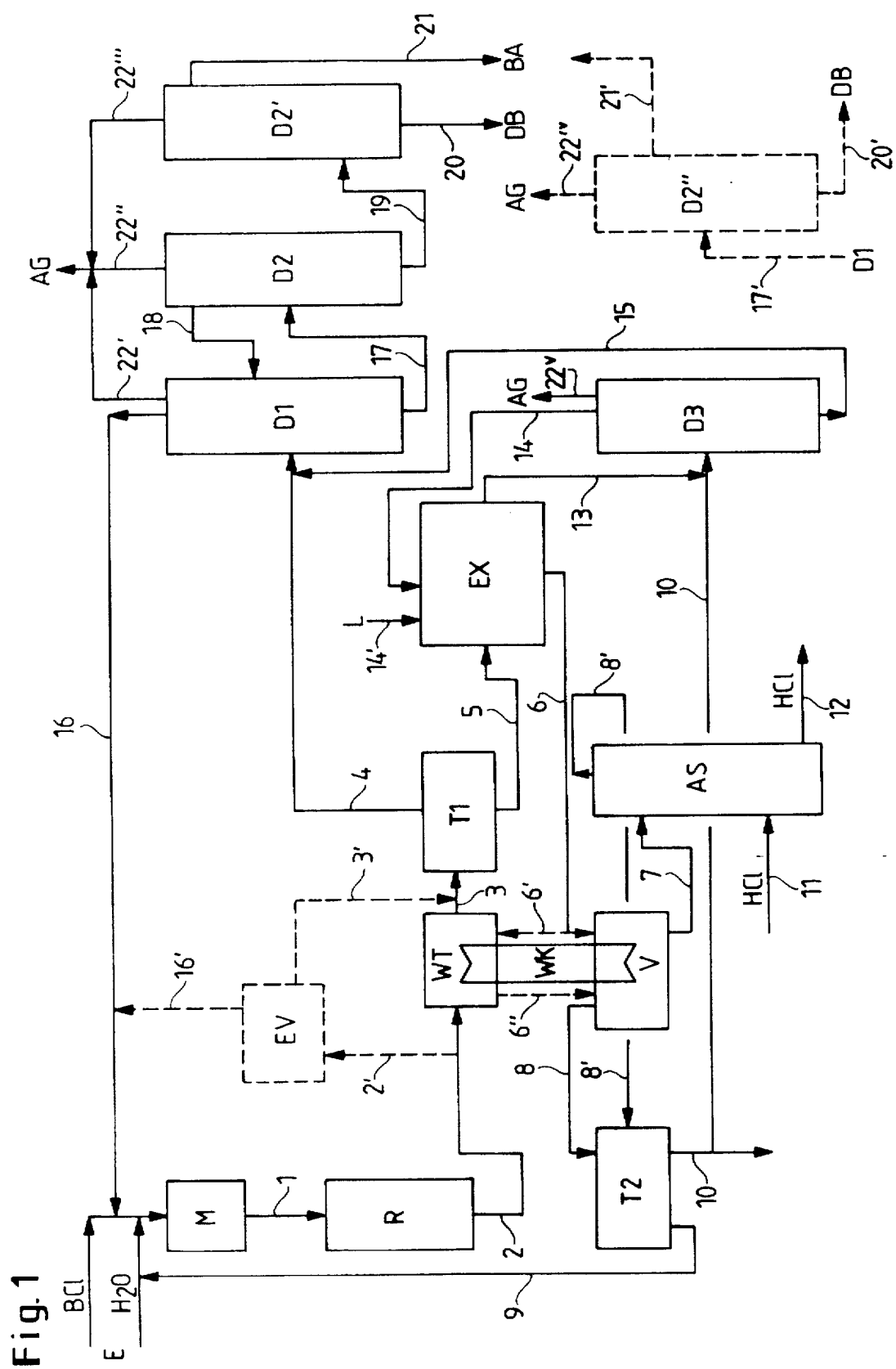

The procedure of this example is described with reference to FIG. 1. The following respective amounts were passed through the unit per hour:

14.01 parts of benzyl chloride (BCl) at approx. 35° C., E,
96.75 parts of water at approx. 150° C., E, in addition 10.51 parts of a mixture 16 at approx. 40° C., the top product of the distillation column D1, comprising approx. 88% benzyl chloride, 4% benzyl alcohol, 6% water and traces of HCl and toluene and about 18.9 parts of a mixture 9 at approx. 40° C., which comprised >99% water and only traces of benzyl chloride and benzyl alcohol and originated from the separation vessel T2, were pumped under a pressure of approx. 10 bar through a mixture M and then through a cascade of 5 stirred tanks, connected in series, equipped with flow baffles and intensively stirred, in which case the temperature increased to 130° C. with good insulation.

After the reaction mixture had left the cascade, it contained approx. 81% water, 6.6% benzyl chloride, 8.5% benzyl alcohol, 0.27% high-boilers (primarily dibenzyl ether) and about 2.9% HCl.

The mixture passed via 2 into the heat exchanger WT, where it was cooled to approx. 90° C., into the separation vessel having a coalescer T1, in which the organic phase settled out from the aqueous phase. The latter (about 121 parts, approx. 94% H$_2$O, 3.3% HCl, 2.6% benzyl alcohol and traces of benzyl chloride, toluene and dibenzyl ether) was extracted with toluene in the extractor Ex, a pulsed column. The exiting aqueous phase 6 containing approx. 96% water, 0.1% benzyl alcohol, 3.4% HCl, some toluene and traces of benzyl chloride was stripped in the evaporator V with the waste heat of the reaction mixture via the heat exchanger WT and further freed from the residual organics, so that it could flow off through 7 into the HCl absorber AS, from which the last traces of organic material were removed via 8' by distillation. These distillates 8' and 8 from V and AS were separated in the separation vessel T2 from the stripped organic compounds 10 (0.15–0.2 parts), which were passed into the column D3 or to Ex. The aqueous phase (>99%) 9 from T2 returned to the mixer M.

Losses of toluene L (0.2–0.4 parts) were replenished from a storage vessel via 14' in Ex.

The toluene extract from Ex passed through 13 to the evaporation column D3, from which toluene passed overhead at 200–250 mbar and then (14) returned to the extraction. The bottom product containing approx. 94% benzyl alcohol, 3.6% high-boilers and remainder residues of toluene and benzyl chloride was, together with the organic phase 4 from T1, fractionated in the column D1.

This organic phase 4 running from the separator T1, apart from the aqueous phase 5, contained the principal amount of the organic reaction product, that is about 19 parts containing approx. 48% benzyl chloride, 46% benzyl alcohol, 1.5% high-boilers, particularly dibenzyl ether, 3.5% water, <1% toluene and about 0.1% HCl. It was worked up, together with the bottom product 15 from the column D3 (approx. 3 parts), by distillation in the distillation column D1. At 100–150 mbar, 10.5 parts passed overhead, which comprised >88% benzyl chloride, approx. 4% benzyl alcohol, 6% water, 1% toluene and the entrained HCl and this was recycled via 16 to the mixer M and thus to the reaction.

About 12.5 parts of crude benzyl alcohol at a content of approx. 97%, 3% of high-boilers and approx. 10 ppm of benzyl chloride ran off from the bottom of the column D1. This bottom product was fed into the column D2 through the feed line 17, in which column the last low-boilers were separated off at 30–40 mbar, which returned via 18 to the column D1. The bottom product from D2 (approx. 11.8 parts) was then pumped through 19 into the column D2' and finally worked up at 30–50 mbar to give high-purity alcohol (11.2–11.3 parts; >99.999% pure). The remaining bottom product (0.5–0.6 parts) still contained about 25% benzyl alcohol which could be isolated in a batchwise vacuum distillation process and could be recycled to column D2 or D2'. This increased the yield to 11.4–11.5 parts.

The high-boiler bottom product 20 could be transferred into benzotrichloride and benzoyl chloride in a chlorination apparatus. There was a small loss, which particularly comprised toluene and water, via the off-gas lines 22' to 22$^V$ and passed to a combustion plant.

14.01 parts/h of benzyl chloride thus produced approx. 11.2 parts of benzyl alcohol/h, or, after recovery of the benzyl alcohol from the bottom product D2', up to 11.5 parts/h.

This corresponds to a yield of 94 to 96% of theory.

Virtually no unusable side-products and by-products were obtained.

We claim:

1. Process for the preparation of benzyl alcohol by hydrolysis of benzyl chloride with water at elevated temperature characterized in that a) benzyl chloride and water are continuously fed into a reactor containing dispersion devices in a molar ratio of 1:(10 to 70), in which reactor a temperature of 80° to 180° C. prevails, and are reacted therein up to a benzyl chloride conversion rate of 30 to 90%, b) the reaction product, after exiting the reactor, is separated in a separator into an aqueous and organic phase, c) the organic phase is separated in a first distillation apparatus into benzyl chloride and crude benzyl alcohol, d) this benzyl chloride is recycled to the reactor, e) the crude benzyl alcohol is refined in a second distillation unit to give high-purity benzyl alcohol, a bottom phase containing the by-products (particularly dibenzyl ether) being produced, f) the aqueous phase from the separator of step b), containing dilute hydrochloric acids is treated in an extraction apparatus with a solvent to extract organic constituents, particularly benzyl alcohol, which are still dissolved in the dilute hydrochloric acid, g) in a third distillation apparatus, this extract is freed of solvent which returns to the extractor, h) the bottom phase from the third distillation is passed to the first, in order to recover the benzyl alcohol therefrom and i) the dilute aqueous hydrochloric acid from the extraction, after taking off residual organics, is passed into an HCl absorption unit in order to recover and concentrate HCl to make high-purity HCl.

* * * * *

UNITED STATES PATENT AND TRADEMARK OFFICE
CERTIFICATE OF CORRECTION

PATENT NO : 5,750,801
DATED : May 12, 1998
INVENTOR(S): Hans-Josef Buysch, et al.

It is certified that error appears in the above-identified patent and that said Letters Patent is hereby corrected as shown below:

Col. 8, Lines 50-51    Delete "(particularly" and substitute --, including--, after "ether" delete ")"

Col. 8, Line 55        Delete "particularly" and substitute --including--

Signed and Sealed this

Fourteenth Day of March, 2000

Attest:

Q. TODD DICKINSON

Attesting Officer    Commissioner of Patents and Trademarks